(12) United States Patent
Kolbe et al.

(10) Patent No.: US 9,303,335 B2
(45) Date of Patent: Apr. 5, 2016

(54) PROCESS FOR PRODUCING CELLULOSIC SHAPED ARTICLES, CELLULOSIC SHAPED ARTICLES AND THE USE THEREOF

(75) Inventors: Axel Kolbe, Neundorf (DE); Hardy Markwitz, Rudolstadt (DE); Sabine Riede, Uhlstaedt-Kirchhasel (DE); Marcus Krieg, Weimar (DE)

(73) Assignee: smartpolymer GmbH, Rudolstadt (DE)

( * ) Notice: Subject to any disclaimer, the term of this patent is extended or adjusted under 35 U.S.C. 154(b) by 547 days.

(21) Appl. No.: 12/742,564

(22) PCT Filed: Nov. 11, 2008

(86) PCT No.: PCT/EP2008/009497
§ 371 (c)(1),
(2), (4) Date: May 12, 2010

(87) PCT Pub. No.: WO2009/062657
PCT Pub. Date: May 22, 2009

(65) Prior Publication Data
US 2011/0045078 A1 Feb. 24, 2011

(30) Foreign Application Priority Data
Nov. 14, 2007 (DE) .......................... 10 2007 054 702

(51) Int. Cl.
| | | |
|---|---|---|
| *A61K 9/14* | (2006.01) | |
| *D01F 1/10* | (2006.01) | |
| *C08L 1/02* | (2006.01) | |
| *C09K 5/06* | (2006.01) | |
| *D01F 2/00* | (2006.01) | |
| *F28D 20/02* | (2006.01) | |
| *A61K 9/16* | (2006.01) | |

(52) U.S. Cl.
CPC ... *D01F 1/10* (2013.01); *C08L 1/02* (2013.01); *C09K 5/063* (2013.01); *D01F 2/00* (2013.01); *F28D 20/023* (2013.01); *A61K 9/1694* (2013.01); *Y10T 428/25* (2015.01); *Y10T 428/2927* (2015.01)

(58) Field of Classification Search
None
See application file for complete search history.

(56) References Cited

U.S. PATENT DOCUMENTS

| | | | |
|---|---|---|---|
| 3,357,845 A * | 12/1967 | Battista | 106/163.01 |
| 4,908,238 A | 3/1990 | Vigo et al. | |
| 5,565,132 A | 10/1996 | Salyer | |
| 5,885,475 A | 3/1999 | Salyer | |
| 2003/0124278 A1 | 7/2003 | Clark et al. | |
| 2004/0126555 A1* | 7/2004 | Hartmann et al. | 428/296.7 |
| 2005/0208300 A1* | 9/2005 | Magill | D01D 5/24 428/364 |
| 2005/0276851 A1* | 12/2005 | Cunningham et al. | 424/468 |
| 2008/0041542 A1* | 2/2008 | Gray et al. | 162/102 |
| 2008/0248704 A1* | 10/2008 | Mathis et al. | 442/102 |

FOREIGN PATENT DOCUMENTS

| | | |
|---|---|---|
| DE | 10 2004 014 704 A1 | 10/2005 |
| EP | 0 745 372 A1 | 12/1996 |
| EP | 1 174 036 A1 | 1/2002 |
| EP | 1 658 395 A1 | 3/2005 |
| WO | WO 99/31141 A2 | 6/1999 |
| WO | WO 01/73188 A1 | 10/2001 |
| WO | WO 03/027365 A1 | 4/2003 |
| WO | WO 2004/081267 A1 | 9/2004 |
| WO | WO 2005/017247 A2 | 2/2005 |
| WO | WO 2006/066291 A1 | 6/2006 |
| WO | WO 2008/040320 A1 | 4/2008 |

OTHER PUBLICATIONS

"Aerosil R 972 Hydrophobic Fumed Silica (Product Information)" May 1, 2005 pp. 1-2.
Xingxiang Zhang, *Heat-storage and thermo-regulated textiles and clothing*, Smart Fibres, Fabrics and Clothing, Woodhead Publishing vol Chapter 3, Jan. 1, 2001 pp. 34-57.

* cited by examiner

*Primary Examiner* — Susan Tran
(74) *Attorney, Agent, or Firm* — ProPat, L.L.C.

(57) ABSTRACT

The invention relates to a process for producing cellulosic shaped articles with stabilized inclusions in a microfine dispersion of nonpolar organic compounds and mixtures by a dry-wet extrusion process. The shaped articles produced in this way exhibit by comparison with unmodified cellulose fibers a substantially increased storage capacity for heat and/or nonpolar active substances. They are suitable in particular for use in textiles for clothing, industrial textiles, leisure, medicine and cosmetics. Potential functional effects imparted include the physical effect of heat storage and/or the uniform and finely meterable storage and release of nonpolar active substances and plant extracts from the interior of the fibers of the shaped articles. It is possible through a suitable choice of the nonpolar portion to produce by this process also fibers capable of absorbing liquid or gaseous nonpolar substances.

26 Claims, 2 Drawing Sheets

PROCESS FOR PRODUCING CELLULOSIC SHAPED ARTICLES, CELLULOSIC SHAPED ARTICLES AND THE USE THEREOF

CROSS-REFERENCE TO RELATED APPLICATIONS

This application is being filed under Rule 1.371 as a National Stage Application of pending International Applicaton No. PCT/EP2008/009497 filed Nov. 11, 2008, which claims priority to patent application German Patent Application No. 10 2007 054 702.3, filed Nov. 14, 2007. Both International Application Nos. PCT/EP2008/009497 and German Patent Application No. 10 2007 054 702.3 are hereby incorporated by reference herein in their entirety.

FIELD OF THE INVENTION

The invention relates to a process for producing cellulosic shaped articles with inclusions of at least one nonpolar organic compound by the dry-wet extrusion process, to a cellulosic shaped article and to the use thereof.

BACKGROUND OF THE INVENTION

It is known that the heat storage capacity of textile fibers and shaped articles can be increased if the shaping polymer is combined with an organic phase change material which can exchange energy with the surrounding area through melting/solidification transition, conformational transition or deorientation/crystallization. The extent of the energy exchange and the effective temperature range correlate with the chemical structure, the change in physical enthalpy and the concentration of the phase change material. It is primarily decisive that the energy exchange effect in the fiber is retained as the result of the molecular near-orientation of the phase change material in or on the shaped article. The following solutions are known:

Firstly, phase change materials are encapsulated with an organic polymer layer and then the capsules are incorporated into a polymer fiber or applied to a fabric (e.g. EP 1 658 395=US 2006/0279017). Micro-encapsulated phase change materials are also used in the examples according to WO 2005/017247 in the production of cellulose fibers having thermoregulatory properties by the Lyocell process. It has proven disadvantageous here that the encapsulation of the phase change material takes place separately from the shaping, or from the processing. Inevitably, a compromise between available capsule batches as regards material and suitability for the shaping process is necessary. In the case of dry-wet extrusion processes, requirements such as fineness and particle size distribution, mechanical and chemical stability, suitability of the phase change material for the field of use, availability and cost, inter alia, are placed on microcapsules.

Furthermore, phase change materials can be incorporated into a polyolefin matrix or a polymer suspension. For example, the production of melt-spun polyolefin fibers which comprise phase change materials having a melting point from 15 to 65° C. is known (U.S. Pat. No. 5,885,475).

The direct incorporation of a phase change material (e.g. a polyethylene glycol) into a hollow fiber is described in U.S. Pat. No. 4,908,238. Here, however, stabilization of the phase change material in the shaped article was dispensed with. From the point of view of the structure, it resembles a microsandwich construction. Simple sandwich structures are disclosed e.g. in US 2003/124278.

According to one particular embodiment in WO 03/027365 (=EP 1 430 169), it should be possible to mix in the PCM during the production of a cellulose fiber in raw form. However, here, no permanent bonding of the PCM to the matrix material (cellulose) can arise, and it is also not possible to spin a fiber from a mixture of PCM and dissolved cellulose.

There is interest in releasing active ingredients from a woven or a cellulose fiber. It is also known to anchor encapsulated, active-ingredient-containing material to the surface of fibers (WO 01/73188) or to incorporate them therein (WO 2006/066291). The possibility of producing fragrances and active ingredients as microcapsules is described e.g. in EP 1 243 326. Again, as a result of the limited availability, the microcapsule has proven to be disadvantageous for industrial application since the encapsulation takes place separately from the shaping.

No approaches are known from the literature as to how the generation of permanent nonpolar organic micro-inclusions into a hydrophilic network-forming polymer, such as cellulose, can be realized by adding the raw materials (solvent, cellulose, nonpolar organic compounds and mixtures, thickeners and phase promoters) to the spinning solution and subsequent shaping in one process. Hitherto, it has also not been described that organic compounds which may be dissolved or suspended in the nonpolar organic compounds and mixtures can be used as modifiers (change in the melting range of phase change materials by e.g. lowering the melting point) or releaseable active ingredients if they were to be incorporated as permanent, nonpolar organic micro-inclusions into a hydrophilic network-forming polymer, such as cellulose.

Only the incorporation of nanoscale active ingredients in powder form and/or of carbon nanotubes was known (WO 2004/081267). Teaching with regard to the incorporation of lipophilic substances into a polar cellulose solution cannot be inferred therefrom.

Proceeding from prior art as described in WO 2006/066291, the object of the invention was accordingly to develop a direct process for producing cellulosic shaped articles with inclusions of nonpolar organic compounds and mixtures utilizing the direct incorporation of these organic, nonpolar compounds and mixtures. If appropriate, these cellulosic shaped articles with inclusions of nonpolar organic compounds should be equipped with further functional additives which are concentrated particularly at or close to the surface of the inclusions.

Moreover, it is within the scope of the object to develop a process in which active ingredients can be dissolved and/or stored in cellulosic shaped articles and can be released to the surrounding area in a controlled manner over a prolonged period.

SUMMARY OF ADVANTAGEOUS EMBODIMENTS OF THE INVENTION

According to the invention, this object is achieved in that an emulsion with at least one nonpolar organic compound in a solution of cellulose in a solvent is prepared and stabilized by adding at least one hydrophobic viscosity-increasing agent, and/or nanoscale, sheet-like and/or elongated, hydro-phobicized particles, for example sheet silicates, nanotubes or nanofilaments, are added to the emulsion; these surround the droplet-like inclusions of the nonpolar organic compound(s) and form a suspension, and the cellulose is recrystallized, giving shaped articles with a cellulose matrix in which the nonpolar organic compound(s) is/are incorporated in disperse form.

DETAILED DESCRIPTION OF ADVANTAGEOUS EMBODIMENTS OF THE INVENTION

Figure 1:
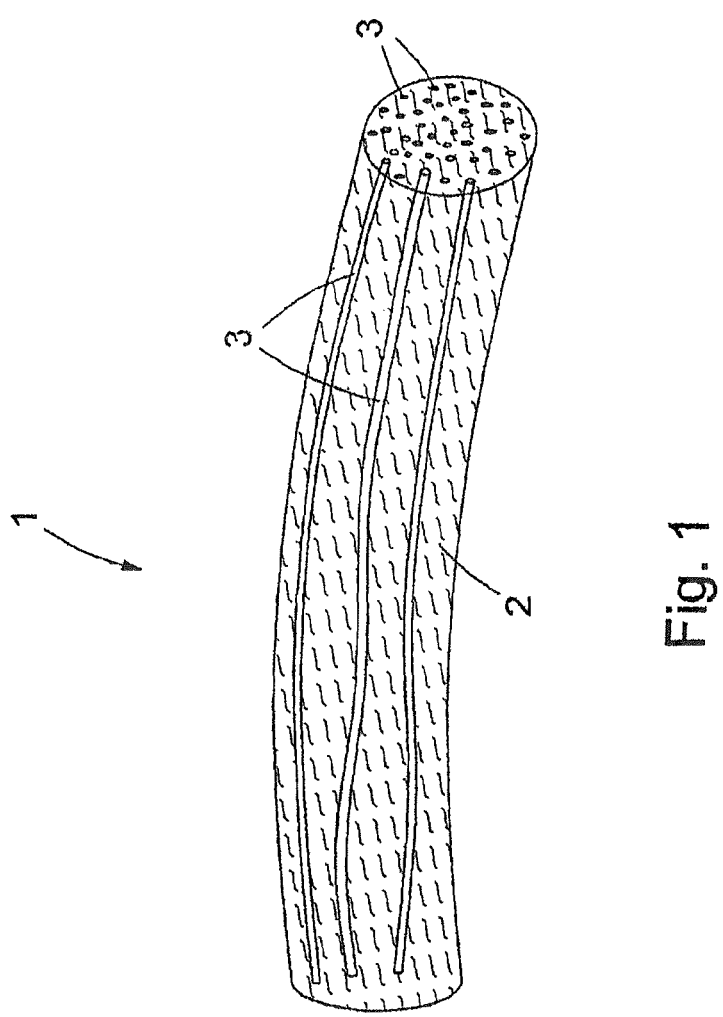
FIG. 1 is a diagrammatic view off an exemplary inventive cellulosic fiber.

In the process, a cellulosic shaping and spinning solution, which can be prepared by dissolving cellulose in a suitable solvent, is admixed with a nonpolar organic material, the viscosity of the nonpolar material is increased so that it can be emulsified in the cellulose solution, and the dispersed phase of the nonpolar material is stabilized. If sheet-like and/or elongated nanoscale particles are added, such as hydrophobicized sheet minerals, e.g. sheet silicates and bentonites, which are exfoliated in the spinning mass, the dispersed phase is surrounded with a layer of these nanoparticles.

Instead of cellulose or in addition to it, any desired polysaccharides in natural or synthetically produced form can be used and/or also mixtures of polysaccharides. Examples are wood cellulose, starch, jute, flax, cotton linters, chitosan or mixtures thereof.

Suitable solvents are, for example, aqueous solutions of tertiary amine oxides, such as N-methylmorpholine N-oxide, and also ionic liquids, preferably ethylmethylimidazolium acetate. It has been found that other ionic liquids are also suitable as solvents for this process, for example 1-butyl-3-methylimidazolium chloride (BMIMCl), 1-ethyl-3-methylimidazolium chloride (EMIMCl), 1-butyl-3-methylimidazolium acetate (BMIMAc) and 1-ethyl-3-methylimidazolium acetate (BMIMAc), N,N-dimethylacetamide lithium chloride, 1-alkyl-3-methylimidazolium salts.

In the process according to the invention, the production and the spinning of a physical solution of the cellulose takes place without derivatization thereof by preparing an emulsion with at least one nonpolar organic compound in a solution of cellulose in N-methylmorpholine N-oxide or an ionic liquid and stabilizing it by adding hydrophobic viscosity-increasing agents (thickeners), and forming a suspension and recrystallizing the cellulose, giving shaped articles with a cellulose matrix in which the nonpolar organic compound is incorporated in disperse form. If appropriate, nanoscale, sheet-like and/or elongated, hydrophobicized particles can be added to the emulsion; these surround the incorporated droplets of the nonpolar organic compound, which leads to further stabilization of the nonpolar material.

When working with ionic liquids, it is of particular interest that the processing of suitable cellulose/salt solutions at temperatures below 90° C. since the spinning dope, in contrast to cellulose/amine oxide solutions, does not solidify and thus remains shapeable in a relatively wide temperature window from room temperature to 120° C. For example, it is thus also possible to process nonpolar materials with a significant vapor pressure at 90° C.

The nonpolar organic compound is preferably a hydrocarbon, a wax, beeswax, an oil, a fatty acid, a fatty acid ester, stearic anhydride, a long-chain alcohol or any desired mixture thereof. It generally has a melting point of less than 100° C. and preferably a melting point in the range from 0 to 40° C. This is also true for the mixtures.

One of the preferred hydrophobic viscosity-increasing agents is a hydrophobicized nanoscale fumed silica. It increases the viscosity of the nonpolar organic compound(s) to the extent that they can be emulsified in the cellulosic shaping and spinning solution. Further suitable thickeners are polymers with olefinic and aromatic moieties, such as, for example, styrene-butadiene block polymers or short-chain polyethylene types or phosphorus-containing esters. These are primarily bicyclic phosphorus-containing esters which additionally offer flame retardancy. Hydrophobicized, nanoscale sheet-like and/or elongated particles can also be used as thickeners. Surprisingly, a fraction of thickeners of from 1 to 50% by weight, preferably from 5 to 20% by weight, based on the weight of the cellulose, suffices to bridge the much greater differences in density and viscosity of an emulsion of hydrocarbons in a cellulosic shaping and spinning solution, compared to hydrocarbon-in-water emulsions. The nanoscale fumed silica generally consists of particles with an average diameter from 30 to 200 nm, preferably from 40 to 100 nm.

Hydrophobicized, nanoscale, fumed silicas suitable for the process according to the invention are known. In the prior art, they serve for the thickening of solutions (EP 0 745 372) and also the stabilization of water-in-oil or oil-in-water emulsions against separation of the disperse phase by positioning the fumed silica at the oil/water interface (DE 10 2004 014 704). They can be used for "controlled release" systems.

The nanoscale, sheet-like, hydrophobicized particles are generally likewise used in a fraction of from 1 to 50% by weight, preferably from 2 to 20% by weight, particularly preferably from 5 to 12% by weight, in each case based on the weight of the cellulose. These are preferably modified sheet silicates, e.g. hydro-phobicized bentonite. The particles generally have a length and width of about 200 to 1000 nm and a thickness of about 1 to 4 nm. The ratio of length and width to thickness (aspect ratio) is preferably about 150 to 1000, preferably from 200 to 500. Hydrophobicized elongated nanoscale particles can likewise be used, for example carbon nanotubes or carbon nanofilaments. Nanotubes generally have a diameter <1 to 30 nm, nanofilaments of ca. 150-300 nm. The length is up to several millimeters.

The nanoscale particles surround the organic material microphases with a layer of nanodisperse structures. The particles have the surprising property that they stabilize the emulsion during shaping and then act as phase promoters between cellulose matrix and enclosed nonpolar organic compounds.

In connection with the present invention, "nanoscale" is used to refer to objects which have, in at least one dimension, a size from 1 to 100 nm, as explained in the industrial standard ISO/TS 27687.

The enclosed nonpolar organic compounds can also be laden with active ingredients. These are nonpolar active ingredients which form solutions or suspensions with the nonpolar organic compounds. The active ingredients are preferably plant products, such as jojoba oil, manoi oil, evening primrose oil, avocado oil, cocoa butter, ethereal plant extracts or nonpolar plant extracts, fat-soluble vitamins, such as vitamin A, D and E, or insecticides, such as pyrethroids, specifically permethrin, or repellents. The concentration of active ingredient(s) can be from 0.001 g per kg up to 500 g and more, preferably from 50 to 150 g per kg of shaped article. The active ingredients can be released into the surrounding area in a controlled manner over a prolonged period. This effect can be demonstrated e.g. using the washing permanency of the functional fibers.

The hydrophobicized nanoscale particles within the cellulosic shaped article can likewise be laden with nonpolar and other organic or inorganic substances. Such organic or inorganic substances include, for example, dyes, pigments, flame retardants, Plasticizers, luminescent substances, UV absorbers, electrically or magnetically conductive substances, matting agents, fragrances, antibacterial active ingredients, fungicides and other functional additives. As a result of weak intermolecular interactions, these molecules are reversibly adsorbed. It is found that excess nanoscale particles preferentially become concentrated at the surface of the shaped article and/or in the vicinity of the surface of the inclusions. This opens up a further option of imparting additional functional properties to the shaped article. As a result of the ability of the cellulose to swell, the shaped articles can also be laden with nonpolar and weakly polar materials after the manufacturing process by nonpolar and weakly polar materials migrating from an aqueous phase to the surface of the nanoparticles, where they are reversibly adsorptively bonded. This procedure is particularly well suited for substances which develop their effect via the gas phase, such as repellents against insects, fragrances of all types or medicinal active substances. Further additives in the shaped bodies may be: dyes, UV stabilizers, bactericidal substances, flame retardants, antistats, crosslinking agents, plasticizers, catalysts.

As the result of adding nonpolar organic compounds and mixtures in a concentration of less than 200% (w/w), based on the weight of the cellulose dissolved in the spinning solution, the shaped articles comprise less than 66% (w/w) of nonpolar organic substances or mixtures.

The process according to the invention leads to cellulosic shaped articles which, compared to unmodified cellulose fibers, have a significantly increased storage capacity for heat and/or nonpolar active substances, and the effect of which can be combined with further functionalities.

Additionally, the melting point of the phase change materials can be lowered by mixing with other organic compounds and thus be adjusted to the value desired in each case. The nonpolar organic compound(s) are also suitable as solvents and/or storage medium for nonpolar organic active ingredients. The active ingredients can be released in a controlled manner from the inclusions in the cellulosic shaped articles. It is also possible to utilize the reverse effect, where the fibers with the inclusions of nonpolar organic substances absorb gaseous and/or liquid nonpolar compounds (harmful substances).

The functional effect is based on the physical effect of heat storage and/or on the uniform and finely doseable storage and release of nonpolar active ingredients, plant extracts and the like from the inside of the fiber. Through appropriate selection of the nonpolar fraction, it is also possible to produce by this process fibers which can serve as absorption medium for liquid or gaseous, nonpolar substances. Further functional modes of action can be achieved through the selection of specific functional thickeners and/or sheet-like nanoscale additives, laden with functional active ingredients.

Using this process it is possible to produce cellulosic shaped articles having the effects already described, such as increased heat storage capacity and "controlled release" functions, much more efficiently and cost-effectively since bulk materials can be processed and conventional encapsulation and incorporation of micro-capsules is dispensed with. The process according to the invention is variable. Thus, e.g. it is possible to utilize the lowering of the melting point of mixtures in order to adapt an industrial standard phase change material exactly to a pregiven application temperature and/or to expand the melting/solidification range.

The shaped articles according to the invention can be processed, especially in the form of fibers, to give textiles which are used in the clothing industry, as industrial textiles and in the leisure sector. Specifically, the shaped articles provided with nonpolar active ingredients can also be used for medicinal or cosmetic purposes. The shaped articles can also serve for producing special papers or films which are laden with active ingredients.

The cellulosic shaped articles according to the invention have a cellulose matrix and inclusions dispersed therein, where the inclusions comprise one or more nonpolar organic compounds stabilized with a hydrophobic thickener.

The nonpolar organic compounds are preferably selected from the group comprising hydrocarbons, waxes, beeswaxes, oils, fatty acids, fatty acid esters, stearic anhydrides and long-chain alcohols, which in each case have a melting point of less than 100° C. The fraction of the nonpolar organic compounds is more than 10% by weight, preferably more than 30% by weight, and particularly preferably more than 40% by weight, based on the weight of the cellulose.

One of the hydrophobic thickeners consists of nanoscale particles, preferably of hydrophobicized nanoscale fumed silica, and is present in an amount of from 1 to 50% by weight, based on the weight of the cellulose.

Moreover, the inclusions can comprise one or more active ingredients from the group comprising plant products, jojoba oil, manoi oil, evening primrose oil, avocado oil, cocoa butter, ethereal plant extracts, nonpolar plant extracts, fat-soluble vitamins, vitamin A, D and E, insecticides, pyrethroids, permethrin and repellents. The active ingredients are present in an amount of up to 50% by weight, based on the weight of the cellulosic shaped article.

In one particular embodiment, the cellulosic shaped article comprises a barrier material made of nanoscale layered particles and/or nanoscale elongated particles, by means of which the nonpolar organic compounds are retained in the inclusions and active ingredients are released in a controlled manner. The fraction of the barrier material is 1 to 50% by weight, based on the weight of the cellulose.

In further embodiments, the cellulosic shaped article has, in a temperature range from 15 to 45° C., a specific latent heat of greater than 20 J/g, preferably of greater than 30 J/g and particularly preferably of greater than 50 J/g.

The invention is illustrated in more detail below by reference to two diagrammatic figures.

FIG. 1 shows a fiber 1 with cellulose matrix 2 and inclusions 3 dispersed therein. The inclusions 3 comprise one or more nonpolar organic compounds which are stabilized with at least one hydrophobic thickener.

Figure 2:
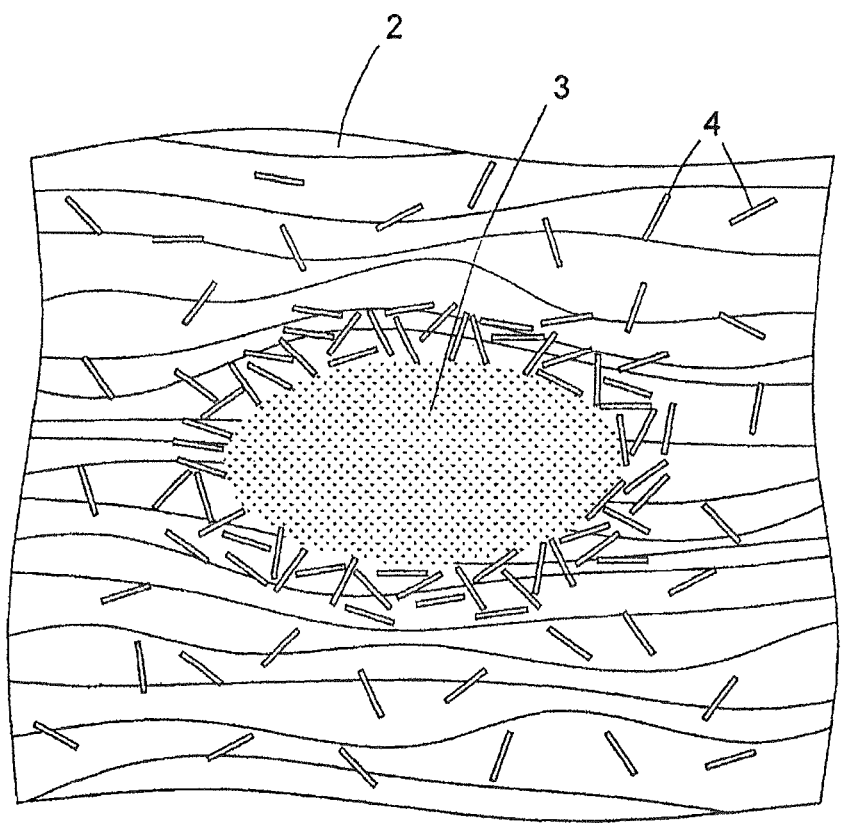
FIG. 2 is a sectional view through an individual inclusion and its surrounding area within the exemplary inventive cellulosic fiber according to FIG. 1.

Details of the inclusions 3 and of the cellulose matrix surrounding them are shown in FIG. 2 in a diagrammatic manner. A barrier material 4 of nanoscale layered particles is dispersed in the cellulose matrix 2. In particular, the layered particles are present separately or exfoliated in the cellulose matrix 2. Around the inclusions 3, the density of the barrier material 4 is increased relative to its mean density in the cellulose matrix 2. Accordingly, the inclusions 3 are surrounded by a zone of the barrier material, through which the nonpolar organic compounds and optionally active ingredients present therein are only able to enter the cellulose matrix 2 via tortuous paths, if at all. Through suitable selection and dosage of the barrier material 4, the permeability for active ingredients can be adjusted in a targeted manner ("controlled release system").

The invention claimed is:

1. A cellulosic extruded article comprising a cellulose matrix and, dispersed therein, inclusions of nonpolar organic compound(s), wherein
said cellulosic extruded article comprises at least one of
(i) a viscosity-increasing hydrophobic agent,
(ii) nanoscale, hydrophobicized sheet particles or
(iii) elongated hydrophobicized particles,
said sheet particles surrounding the inclusions as barrier material,
the nonpolar organic compound(s) is present in an amount of more than 10% by weight, based on the weight of the cellulose matrix, and
the hydrophobicized sheet particles are modified sheet silicates;
wherein the barrier material consists of hydrophobicized bentonite;
the nonpolar organic compound(s) have a melting point of less than 100° C. and is/are selected from the group consisting of hydrocarbons, waxes, beeswaxes, oils, fatty acids, fatty acid esters, stearic anhydrides and long-chain alcohols,
the hydrophobic viscosity increasing agent(s) is present in an amount of 1 to 50% by weight, based on the weight of the cellulose matrix, and
said article has a specific latent heat of greater than 20 J/g in a temperature range from 15 to 45° C.

2. A cellulosic extruded article comprising a cellulose matrix and, dispersed therein, inclusions of nonpolar organic compound(s), wherein
said cellulosic extruded article comprises at least one of
(i) a viscosity-increasing hydrophobic agent,
(ii) nanoscale, hydrophobicized sheet particles or
(iii) elongated hydrophobicized particles,
said sheet particles surrounding the inclusions as barrier material,
the nonpolar organic compound(s) is present in an amount of more than 10% by weight, based on the weight of the cellulose matrix, and wherein
the barrier material consists of hydrophobicized bentonite;
active ingredients are present in an amount of up to 50% by weight, based on the weight of the cellulosic article,
the hydrophobic viscosity increasing agent(s) is present in an amount of 1 to 50% by weight, based on the weight of the cellulose matrix, and
said article has a specific latent heat of greater than 20 J/g in a temperature range from 15 to 45° C.

3. The cellulosic extruded article as claimed in claim 1, wherein the nonpolar organic compound(s) have a melting point of less than 100° C. and is/are selected from the group consisting of hydrocarbons, waxes beeswaxes, oils, fatty acids, fatty acid esters, stearic anhydrides and long-chain alcohols.

4. A cellulosic extruded article as claimed in claim 2 comprising a cellulose matrix and, dispersed therein, inclusions of nonpolar organic compound(s), wherein said cellulosic extruded article comprises at least one viscosity-increasing, hydrophobic agent and/or nanoscale hydrophobized sheet particles and/or elongated hydrophobicized particles that surround the inclusions as barrier material,
wherein the nonpolar organic compound(s) is a plant product active-ingredient and/or contains one or more active ingredients selected from the group consisting of fat-soluble vitamins, insecticides and repellents,
and said article has a specific latent heat of greater than 20 J/g in a temperature range from 15 to 45° C.

5. The cellulosic extruded article as claimed in claim 4, wherein the active ingredients are present in an amount of up to 50% by weight, based on the weight of the cellulosic article.

6. The cellulosic extruded article as claimed in claim 1, wherein the hydrophobic viscosity increasing agent(s) is present in an amount of 1 to 50% by weight, based on the weight of the cellulose matrix.

7. The cellulosic extruded article as claimed in claim 1, wherein the hydrophobic viscosity-increasing agent consists of hydrophobicized nanoscale fumed silica.

8. The cellulosic extruded article as claimed in claim 1, wherein the barrier material is present in an amount ranging from 1 to 50% by weight, based on the weight of the cellulose.

9. The cellulosice extruded article as claimed in claim 1, wherein the inclusions are surrounded by a zone with increased density of the barrier material.

10. The cellulosic extruded article as claimed in claim 1, wherein said article is a fiber and said fiber comprises viscosity-increasing, hydrophobic agent and barrier material consisting of hydrophobicized bentonite sheet particles, said sheet particles having a length and width of about 200 to 1000 nm and a thickness of 1 to 4 nm, and the fiber, according to a test in accordance with DIN EN 26330 (1993), the loss of one or more nonpolar organic compounds after 20 washes is less than 20% by weight, based on the amount of respective organic compound originally present in the fiber.

11. The cellulosic extruded article as claimed in claim 1, wherein said hydrophobic viscosity-increasing agent comprises phosphorus-containing esters and/or hydrophobicized nanoscale particles laden with flame retardants imparting a flameproof finish.

12. Textile sheet materials, papers or films comprising cellulosic articles as claimed in claim 1, wherein said textile sheet materials are optionally blended with other textile fibers and said papers or films optionally further comprise active ingredients.

13. The cellulosic extruded article as claimed in claim 1, wherein the fraction of nonpolar organic compound(s) is more than 30% by weight, based on the weight of the cellulose matrix.

14. The cellulosic extruded article as claimed in claim 4, wherein the plant products are selected from jojoba oil, manoi oil, evening primrose oil, avocado oil, cocoa butter, ethereal plant extracts, or nonpolar plant extracts, the fat-soluble vitamins are selected from vitamin A, D or E, and the insecticides are pyrethroids.

15. The cellulosic extruded article as claimed in claim 1, wherein said article has a specific latent heat of greater than 50 J/g in a temperature range from 15 to 45° C.

16. The cellulosic extruded article as claimed in claim 1, wherein said cellulosic extruded article comprises (i) said viscosity-increasing agent and (ii) said nanoscale sheet and/or elongated hydrophobicized particles.

17. The cellulosic extruded article as claimed in claim 1, wherein tire nonpolar organic compound is selected from the group consisting of hydrocarbons, waxes, beeswaxes, oils, fatty acids, fatty acid esters, stearic anhydrides and long-chain alcohols and the fraction of nonpolar organic compound(s) is more than 40% by weight, based on the weight of the cellulose.

18. The cellulosic extruded article as claimed in claim 1, wherein the cellulosic extruded article is a fiber, a paper or a film.

19. The cellulosic extruded article as claimed in claim 18, wherein the cellulosic extruded article is a fiber and said fiber includes at least one hydrophobic, viscosity-increasing agent as stabilizer and nanoscale, sheet-like and/or elongated, hydrophobicized particles as barrier material.

20. A process for producing cellulosic shaped articles as claimed in claim 1 with inclusions of at least one nonpolar organic compound by the dry-wet extrusion process, said process comprising
    preparing an emulsion with at least one nonpolar organic compound in a solution of cellulose in a solvent and stabilizing said emulsion by adding at least one hydrophobic viscosity-increasing agent, and/or
    adding nanoscale, sheet-like hydrophobicized bentonite and/or elongated, hydrophobicized particles to the emulsion that surround droplet-like inclusions of the nonpolar organic compound(s) and form a suspension, and
    recrystallizing the cellulose to produce shaped articles with a cellulose matrix in which the nonpolar organic compound(s) is/are incorporated in disperse form.

21. The process as claimed in claim 20, wherein the nanoscale particles are hydrophobic viscosity-increasing agents, the sheet-like, hydrophobicized particles are hydrophobicized bentonites and the elongated particles are nanotubes or nanofilaments.

22. The process as claimed in claim 20, wherein the hydrophobic agent is nanoscale structured, fumed silica or polymers with olefinic and aromatic moieties.

23. The process as claimed in claim 20, wherein the solvent is a tertiary amine oxide or an ionic liquid.

24. The process as claimed in claim 21, wherein the hydrophobic agents are present in an amount ranging from 1 to 50% by weight, based on the weight of the cellulose.

25. The process as claimed in claim 21, wherein the modified sheet silicates are hydrophobicized bentonites.

26. The process as claimed in claim 20, wherein dyes, UV stabilizers, bactericidal substances, flame retardants, antistats, crosslinking agents, plasticizers and/or catalysts are added both to the hydrophobic agent(s) and also the sheet-like nanoparticles.

* * * * *